United States Patent [19]

Sorkin

[11] Patent Number: 5,069,228

[45] Date of Patent: Dec. 3, 1991

[54] CONDOM WITH PROXIMAL PUBIC SHIELD

[76] Inventor: Reuben Sorkin, 4721 University Dr., Coral Gables, Fla. 33146

[21] Appl. No.: 579,904

[22] Filed: Sep. 10, 1990

Related U.S. Application Data

[63] Continuation-in-part of Ser. No. 93,933, Sep. 8, 1987, abandoned, and Ser. No. 110,152, Oct. 19, 1987, Pat. No. 4,856,534, and Ser. No. 148,724, Jan. 25, 1988, Pat. No. 4,808,174, and Ser. No. 327,796, Mar. 23, 1989, Pat. No. 4,955,392.

[51] Int. Cl.⁵ .............................................. A61F 5/44
[52] U.S. Cl. ..................................... 128/844; 604/352
[58] Field of Search ................ 128/844, 918; 604/352

[56] References Cited

U.S. PATENT DOCUMENTS

| | | | |
|---|---|---|---|
| 2,123,343 | 7/1938 | Rightsell | 128/844 |
| 2,305,453 | 12/1942 | Martos | 128/844 |
| 4,794,920 | 1/1989 | Robichaud | 128/844 |
| 4,808,174 | 2/1989 | Sorkin | 604/352 |
| 4,856,534 | 8/1989 | Sorkin et al. | 128/844 |
| 4,872,464 | 10/1989 | Loeb et al. | 128/844 |
| 4,888,007 | 12/1989 | Loeb et al. | 128/844 |

Primary Examiner—Noah P. Kamen
Attorney, Agent, or Firm—Malloy, Downey & Malloy

[57] ABSTRACT

A condom of rubbery material such as latex which includes a tubular length having a closed first end and an open second end and an integral pubic shield about the open end with the tubular length being sized to receive and snugly jacket the penis of a user and the pubic shield being adapted to overlay the pubic area of a user and including adhesive means to attach the shield in protective covering relation of the pubic area of a user about the base of the penis.

5 Claims, 2 Drawing Sheets

CONDOM WITH PROXIMAL PUBIC SHIELD

This application is a continuation-in-part of earlier filed U.S. Patent Application No. 07/093,933, filed Sept. 8, 1987, now abandoned; U.S. Ser. No. 07/110,152, filed Oct. 19, 1987, now U.S. Pat. No. 4,856,534, dated Aug. 15, 1989; U.S. Ser. No. 07/148,724, filed Jan. 25, 1988, now U.S. Pat. No. 4,808,174, dated Feb. 28, 1989; and U.S. Ser. No. 07/327,796, filed Mar. 23, 1989, now U.S. Pat. No. 4,955,392.

FIELD OF THE INVENTION

This invention relates to a condom which includes a proximal pubic shield; the condom is of a rubbery material, such as latex, and the shield is sized to overlay the pubic area and is provided with an adhesive to temporarily adhere to the pubic area.

BACKGROUND OF THE INVENTION

There is a growing awareness of the seriousness of sexually transmitted diseases and the need for protection. Defects of conventional condoms have become increasingly apparent. For example, it is estimated that about one-sixth of the users of condoms may, nevertheless, incur sexually transmitted diseases because of improper use. This invention is of a condom of thin rubbery and pliable material, such as latex, with an integral pubic shield which reduces the risk of sexually transmitted diseases and provides extra prevention. This is highly desirable especially in view of the seriousness of diseases such as AIDS, Herpes, Syphilis, Gonorrhea, Chalasmydia and other sexually transmitted diseases.

There are deficiencies in conventional prior art tubular condoms in that the same may slip off the male organ after ejaculation because the penis becomes flaccid and shrinks to its normal size. When this happens, both partners are exposed to sexually transmitted diseases as well as pregnancy. Because the vagina provides an ideal growth culture media for all kinds of venereal disease, vaginal fluids should be avoided. The ordinary tubular condom does not provide a water-tight seal at the base to protect the pubic area of a user from exposure of his body to sexually transmitted diseases. This invention provides a pubic shield portion integral with a tubular condom portion, which shield is sized to overlay the pubic area of a user and which is provided with an adhesive to adhere the shield in protective covering relation of the pubic area during use. This invention takes advantage of the favorable properties of conventional materials, such as latex, which, in general, are characterized by a good appearance and good feel. This invention does not utilize fiber reinforcement of the condom or plastic materials which are relatively strong but do not have a history of use in the condom art. It is recognized that long term use of new materials may have deleterious effects, such as prior art products used by females during menstruation which were later found to cause toxic shock syndrome.

In the past, reinforced tubular lengths for shielded condoms, or tubular condoms of oversize or materials different than rubbery material, such as latex, have been taught, it being accepted that if a pubic shield is provided, and especially if adhered to the pubic area, the tubular length would have to be a) stronger or b) modified as to shape in order to avoid puncture or breaking of the tubular portion. In other words, it was accepted that if conventional condom materials, such as latex were used to provide a thin pliable condom with a good "feel," a pubic shield should not be provided for the tubular length unless it were modified by thickening the material of the tubular length, reinforcing it with fiber or increasing its size as in U.S. Letters Pat. No. 4,794,920. In effect, the prior art has been taught a pubic shield integral with a condom tubular length but at the cost of a loss of "feel" or sensitivity to the user. Applicant has discovered that, although the tubular length condom portion is of thin conventional rubbery material that preserves "feel," a pubic shield with adhesive to secure it to the pubic area of a user is possible and may be provided to increase protection without sacrifice of the sensitivity or "feel" of conventional condom materials.

OBJECT OF THE INVENTION

It is, therefore, an object of this invention to provide an improved thin-walled condom of rubbery material such as latex which comprises a) a tubular portion having a closed distal end and an open proximal end with the proximal end spaced from the distal end such that the tubular portion is of a length sized to snugly and protectively jacket the penis of a user; b) a pubic shield integral with the tubular portion so that the pubic shield provides protection for an enlarged zone about the base of the penis; and c) an adhesive applied to the pubic shield for attachment of it to the body of a user during coitus.

It is a general object of this invention to provide an improved condom of rubbery material as described more fully hereinafter which is inexpensive to manufacture, well adapted for avoiding sexually transmitted diseases and which is highly desirable to avoid sexually transmitted diseases and which does not sacrifice sexual sensitivity.

In accordance with these and other objects which will become apparent hereinafter, the instant invention will now be described with reference to the accompanying drawings in which:

DETAILED DESCRIPTION OF THE PREFERRED EMBODIMENT

Figure 1:
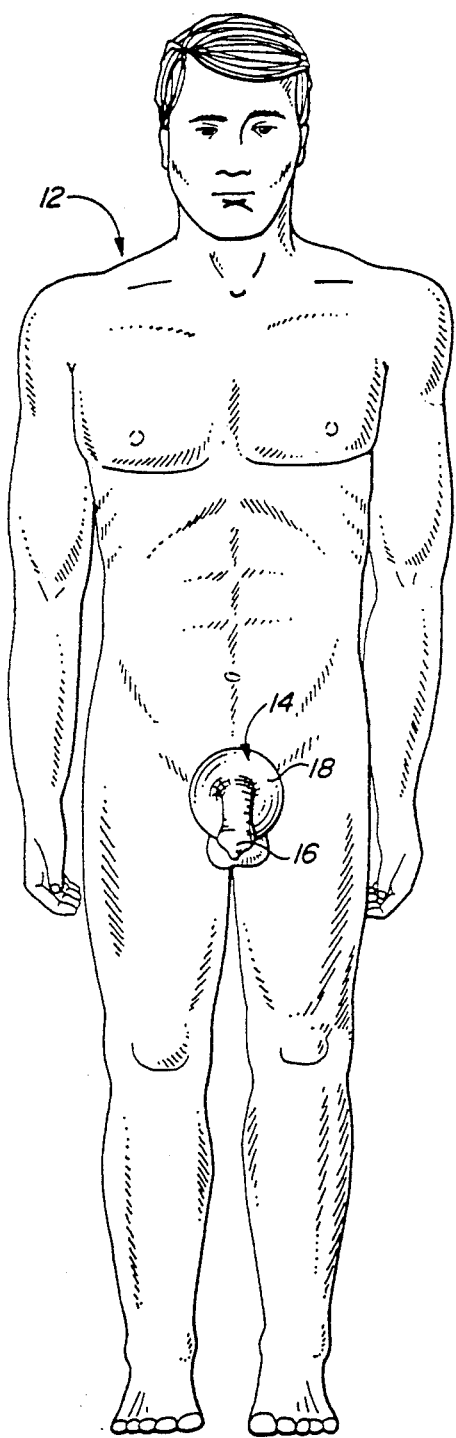
FIG. 1 illustrates the improved condom on the body of a wearer.
Figure 2:
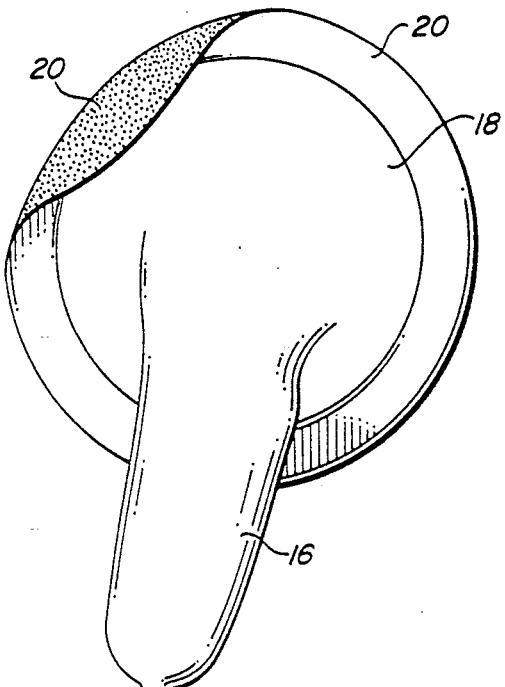
FIG. 2 illustrates the condom prior to use.
Figure 3:
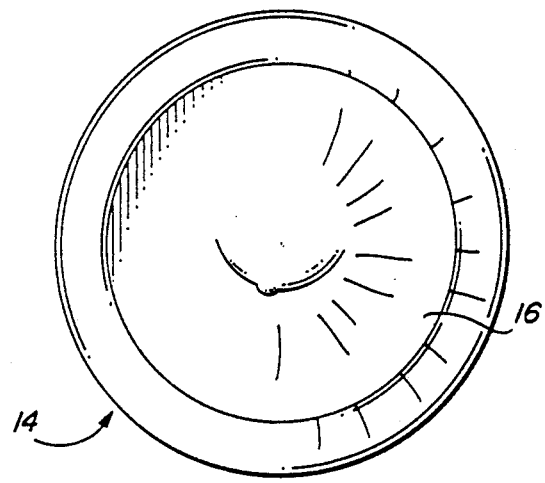
FIG. 3 illustrates the condom in a rolled condition.
Figure 4:
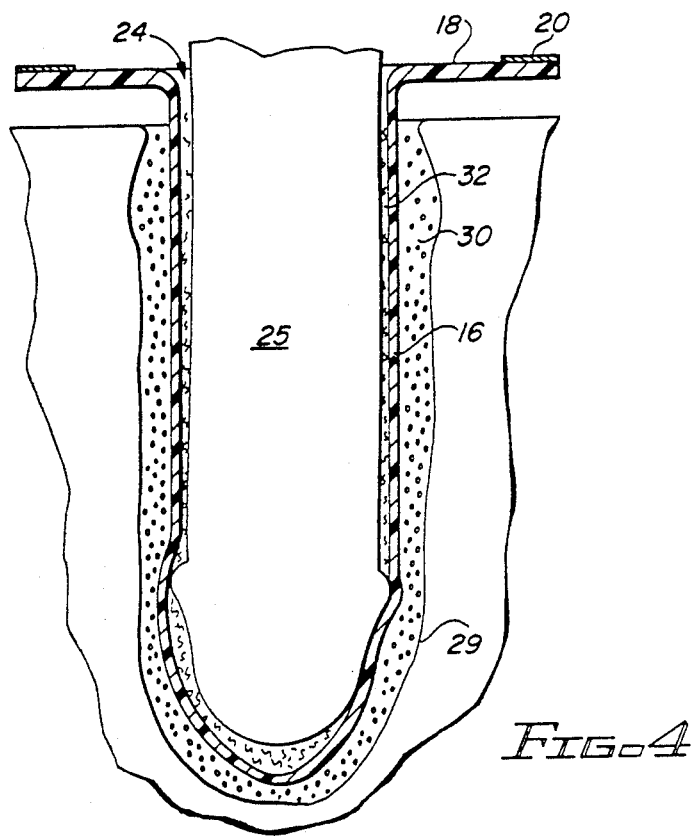
FIG. 4 illustrates the condom in use.

The present invention relates to an improved condom of rubbery material such as latex which includes an integral pubic shield. FIGS. 1 and 2 illustrate one embodiment of the invention. In FIG. 3, the condom is shown rolled upon itself. It may, however, be provided in packages in a collapsed attitude similar to the package used for surgical gloves, for example. Preferably, the condom is provided in three sizes, small, medium and large.

In the several views, the numerals designate similar parts in the several figures.

The present invention includes a tubular length of rubbery material such as latex which can be stretched substantially beyond its original length and, when relaxed, it will return to its original length.

In FIG. 1, a condom 14 of the type to be described is shown on a wearer 12. The condom 14 includes a tubular portion 16, see FIG. 2. It has a rounded, closed distal end that may include a smaller diameter reservoir portion at the terminal end zone. Also, the condom includes an integral pubic shield 18 that is shown in a rolled state in FIG. 3. In FIG. 3, the condom 14 is rolled onto itself and in FIG. 2, is shown in an unrolled attitude.

FIG. 1 shows the condom 14 disposed on the male user 12 In that figure, the pubic shield 18 is seen to protect the pubic area of the user. The tubular portion 16 has an open proximal end for inserting the penis 25 into a female opening 24. A lubricant may be utilized on the exterior surface of the tubular portion 16 and, if desired, within the tubular portion.

The shield 18 extends radially outwardly from the tubular portion 16 at the proximal end at least a distance from one and one-half times the diameter of the opening at the proximal end. Preferably, the radial span of the shield is at least 2½ inches. The shield includes adhesive means to adhere it to the pubic area of a user about the base of the penis during and after intercourse.

In addition to protecting the user from contact with vaginal and other fluids 30 within the vagina 29 during intercourse, after ejaculation and the collapse of the penis, the shield will better trap the ejaculated fluids and thereafter protect the other sexual partner from the male fluids 32.

Figure 5:
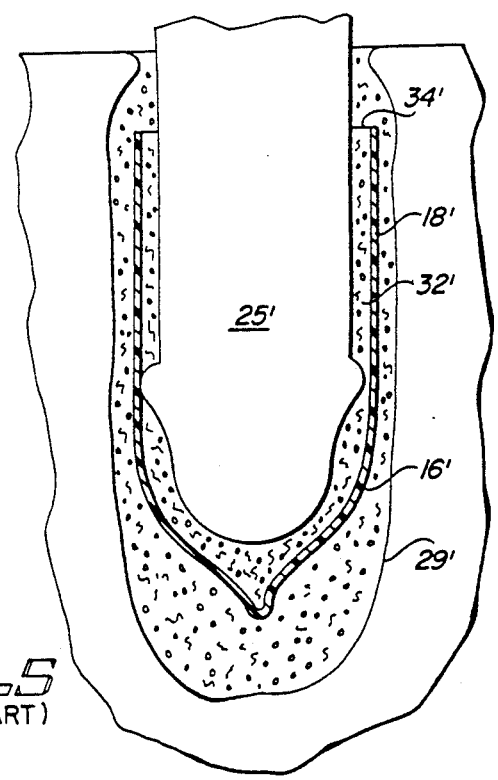
FIG. 5 is illustrative of problems which can occur with prior art condoms which do not have a pubic shield.

Referring to FIG. 5, when the penis becomes flaccid, the terminal end zone of a conventional condom 16', which does not have a shield, may creep into the vagina 29' in which event, the male fluids 32' may mix as at 34' with the vaginal fluids as the penis 25' becomes flaccid. The adhesive and the shield structure of this invention guard against this happening. With the present invention, during and after coitus, use of the condom of the present invention prevents exposure of the penis, vagina and pubic areas to infection. The adhesive 20 may be applied as a ring, preferably, about the outer periphery of the shield. Also, a removable liner indicated also by the numeral 20, since it is transparent, overlays the adhesive. Preferably, the adhesive is of the type which is readily peeled from the body without pain. Such an adhesive or skin glue, as it is sometimes called in the field, is a copolymer of an acrylic ester and acrylic acid. The adhesive is painless on removal.

The material such as that utilized in the manufacture of the foregoing condom structure is preferably translucent, is relatively thin and provides a strong condom without sacrificing a "good feel."

In use with this condom, the penis is at all times out of contact with vaginal secretions which may contain infectious organisms. The integral shield portion, being adhesively attached to the pubic area, protects the pubic area about the base of the penis of a user. A suitable painless adhesive may be used such as one which is commercially available from the Johnson & Johnson Company of New Brunswick, N.J., known as a First Aid Adhesive. Preferably, the condom is provided in three sizes, small, medium and large. The shield is a circular disk preferably of about five inches in diameter and is an integral part of the condom. Preferably, a liner is provided for the adhesive which can be peeled away.

What is claimed is:

1. A condom of thin pliable rubbery latex material comprising:
   a sleeve having an open proximal end and a closed proximal end having a reduced diameter defining a reservoir, said sleeve being sized to receive and snugly jacket an erect penis,
   a pubic shield integrally formed with said sleeve having a uniform thickness of the pliable rubbery latex material and extending radially away from the proximal end being structured and disposed to overlay the pubic area of a user during intercourse,
   said shield having a surface adapted to confront the pubic area about the base of a penis of a user, and
   adhesive means comprising a skin compatible glue formed from a co-polymer of an acrylic ester and acrylic acid, said adhesive means being disposed on the surface to adhere the shield to the pubic area of the user during intercourse.

2. A condom as set forth in claim 1 wherein liner means are provided to protectively overlay the adhesive means prior to use and to be peeled away for use.

3. A condom as set forth in claim 2 wherein the shield is generally circular and of an overall diameter of about five inches.

4. A condom as set forth in claim 1 wherein the shield is generally circular and of an overall diameter of about five inches.

5. A condom as set forth in claim 1 wherein the shield has a peripheral zone and said adhesive means are provided on the peripheral zone.

* * * * *